(12) United States Patent
Blake et al.

(10) Patent No.: US 10,537,892 B2
(45) Date of Patent: Jan. 21, 2020

(54) SAMPLE TUBE WITH INTEGRATED MIXING PLUNGER HEAD

(71) Applicant: Illumina, Inc., San Diego, CA (US)

(72) Inventors: James Christopher Blake, La Jolla, CA (US); Umberto Ulmanella, San Diego, CA (US); Bradley Kent Drews, Poway, CA (US); Michael Dai Wang, San Diego, CA (US); Stephen Wayne Clark, San Diego, CA (US); Michael Adalbert Niziolek, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 56 days.

(21) Appl. No.: 15/841,113

(22) Filed: Dec. 13, 2017

(65) Prior Publication Data

US 2018/0185840 A1 Jul. 5, 2018

Related U.S. Application Data

(60) Provisional application No. 62/441,921, filed on Jan. 3, 2017.

(51) Int. Cl.
*B01L 3/00* (2006.01)
*A61B 10/00* (2006.01)
*B65D 25/08* (2006.01)

(52) U.S. Cl.
CPC ...... *B01L 3/50825* (2013.01); *A61B 10/0045* (2013.01); *B01L 3/502* (2013.01); *B65D 25/085* (2013.01)

(58) Field of Classification Search
CPC .. B01L 3/50825; B01L 3/502; A61B 10/0045; B65D 25/085
(Continued)

(56) References Cited

U.S. PATENT DOCUMENTS 4,466,298 A    8/1984  Tervamaeki et al.
4,479,578 A *  10/1984 Brignola ............... A61J 1/2093
                                                          206/221
(Continued)

FOREIGN PATENT DOCUMENTS

EP    3040721    7/2016
RU    2672450    11/2018
(Continued)

OTHER PUBLICATIONS

PCT/US2017/067833 "International Search Report and Written Opinion," dated Apr. 17, 2018, 8 Pages.
(Continued)

*Primary Examiner* — Sean E Conley
*Assistant Examiner* — Jacqueline Brazin
(74) *Attorney, Agent, or Firm* — Illumina, Inc.

(57) ABSTRACT

Disclosed herein are devices and techniques for providing for enhanced fluid mixing in a sample vial. A plunger head may be removably housed inside of a cap that is attached to a container; the cap may have an opening allowing a shaft, e.g., a probe or sipper shaft, to be inserted into the cap and into the plunger head. The shaft may be used to push the plunger head free of the cap, and then to reciprocate the plunger head within the container to mix the content. Withdrawal of the shaft may then cause the plunger head to disengage from the shaft and remain in the container.

20 Claims, 8 Drawing Sheets

(58) Field of Classification Search
USPC .......................................................... 422/568
See application file for complete search history.

(56) References Cited

U.S. PATENT DOCUMENTS

| | | | |
|---|---|---|---|
| 5,823,373 | A | 10/1998 | Sudo et al. |
| 6,230,884 | B1 | 5/2001 | Coory |
| 2015/0297457 | A1* | 10/2015 | Buder .................. A61J 1/2003 |
| | | | 222/252 |
| 2015/0344203 | A1 | 12/2015 | Anderson |
| 2016/0187306 | A1 | 6/2016 | Pohl et al. |
| 2016/0242674 | A1 | 8/2016 | Ahmad et al. |
| 2016/0258849 | A1 | 9/2016 | Murayama et al. |
| 2016/0279030 | A1* | 9/2016 | Giraud ............... B65D 51/2835 |
| 2016/0303397 | A1 | 10/2016 | Hirschman et al. |
| 2016/0304821 | A1 | 10/2016 | Ito |
| 2017/0157316 | A1* | 6/2017 | Browne ................ A61M 5/001 |

FOREIGN PATENT DOCUMENTS

| | | |
|---|---|---|
| SU | 1165224 | 6/1985 |
| WO | 2014/090776 | 6/2014 |
| WO | WO 2014/090776 | 6/2014 |
| WO | 2015177004 | 11/2015 |

OTHER PUBLICATIONS

International Search Report and Written Opinion dated Apr. 17, 2018 for International Application No. PCT/US17/067833.

\* cited by examiner

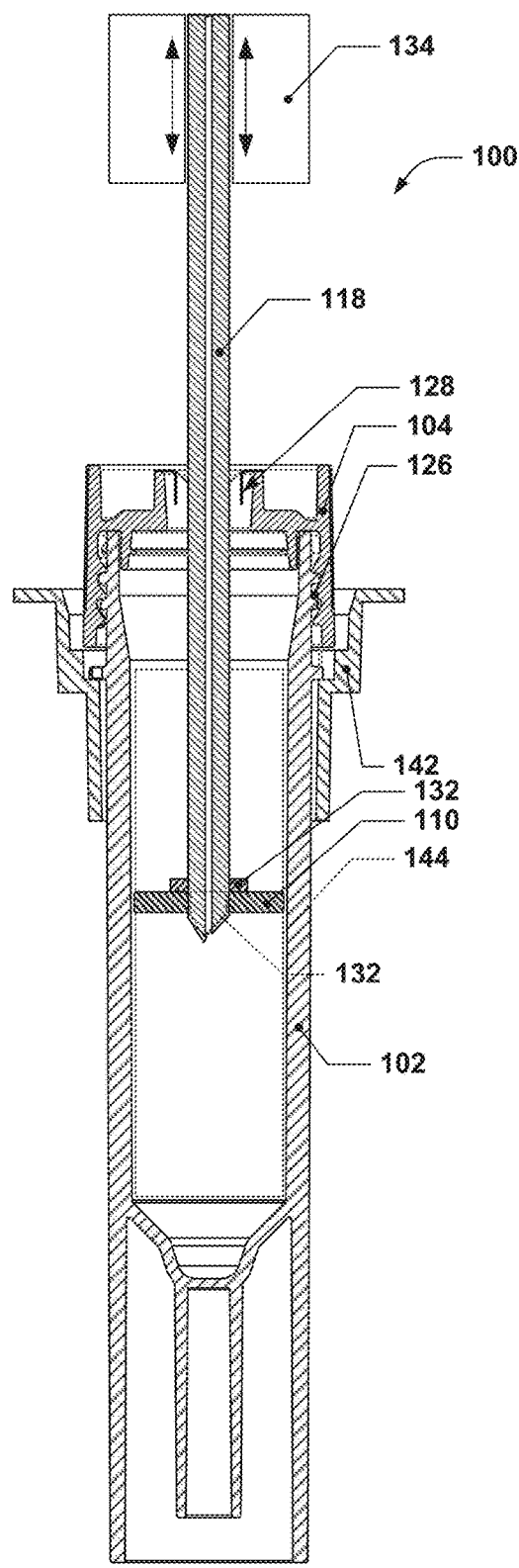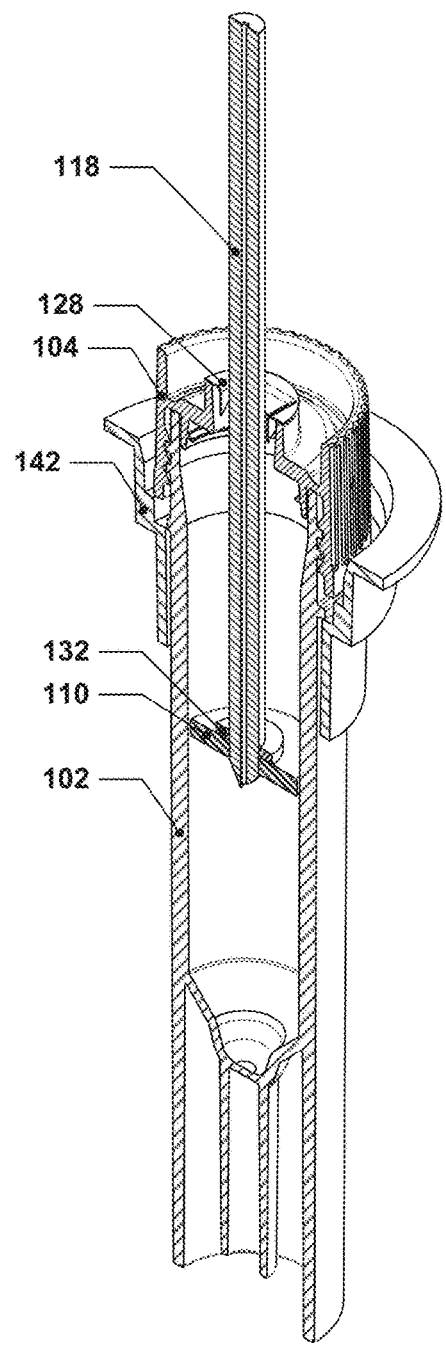
Figure 3  Figure 3'

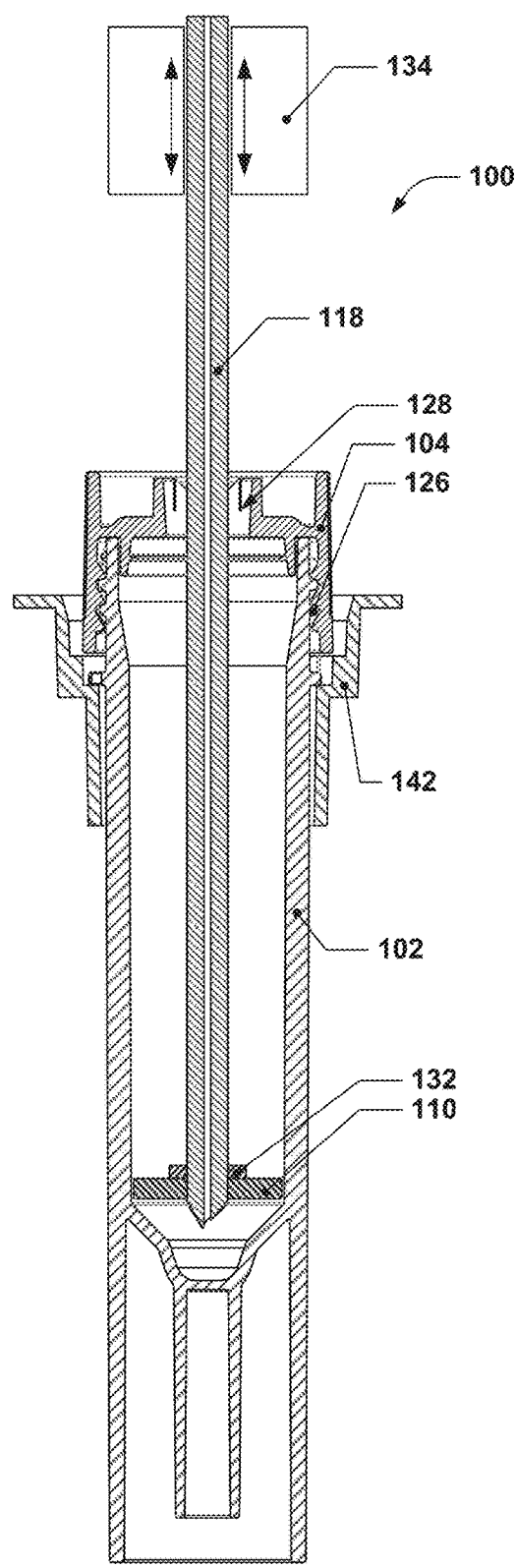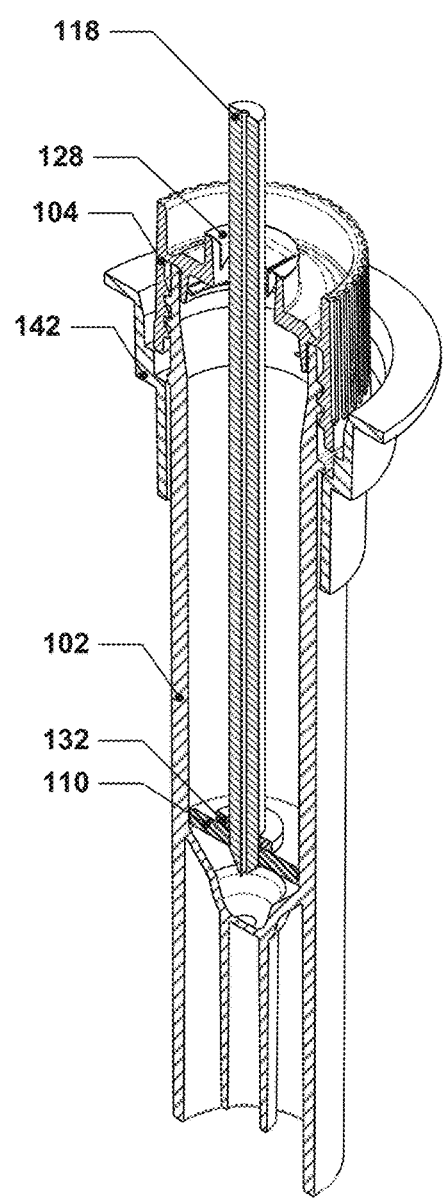
Figure 4
Figure 4'

Figure 6"

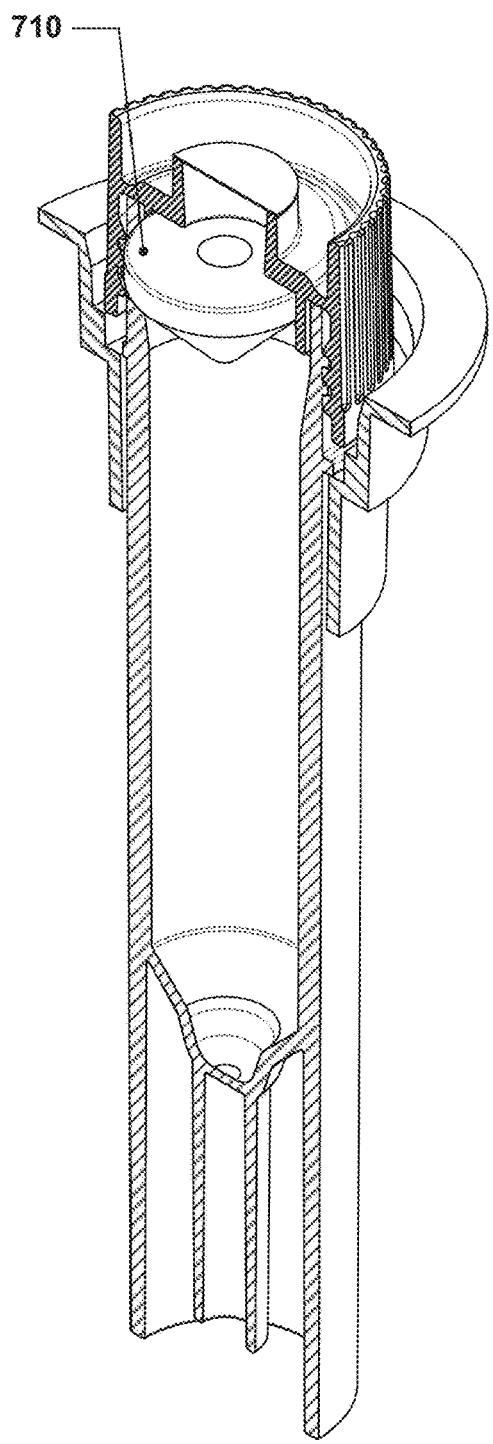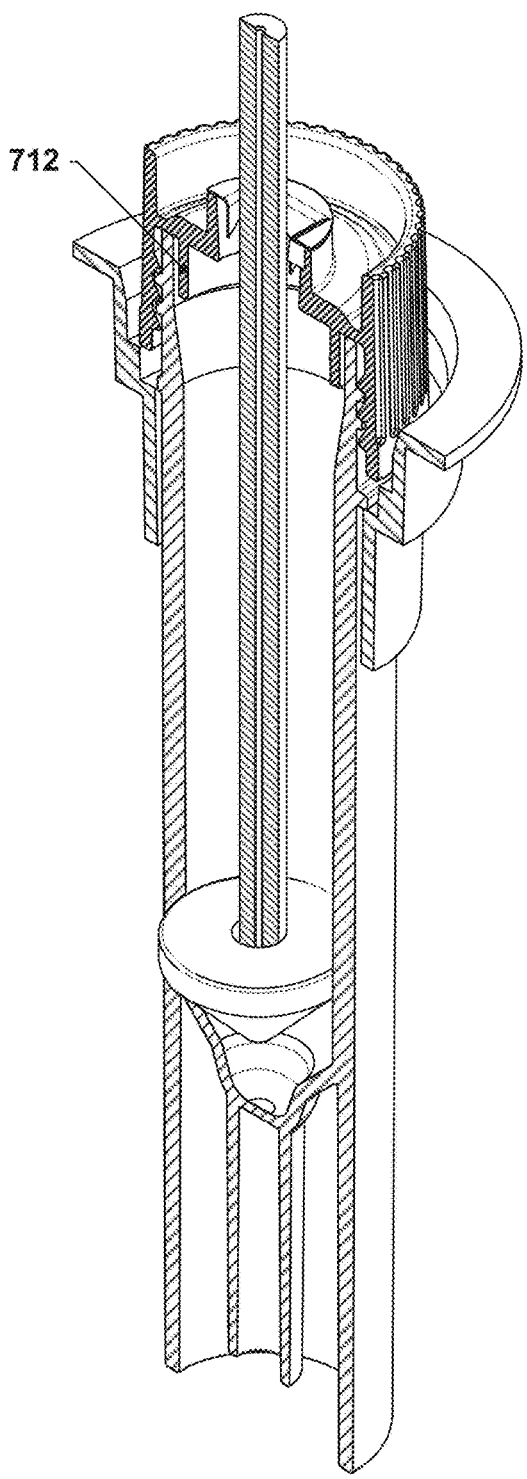
Figure 7     Figure 7'

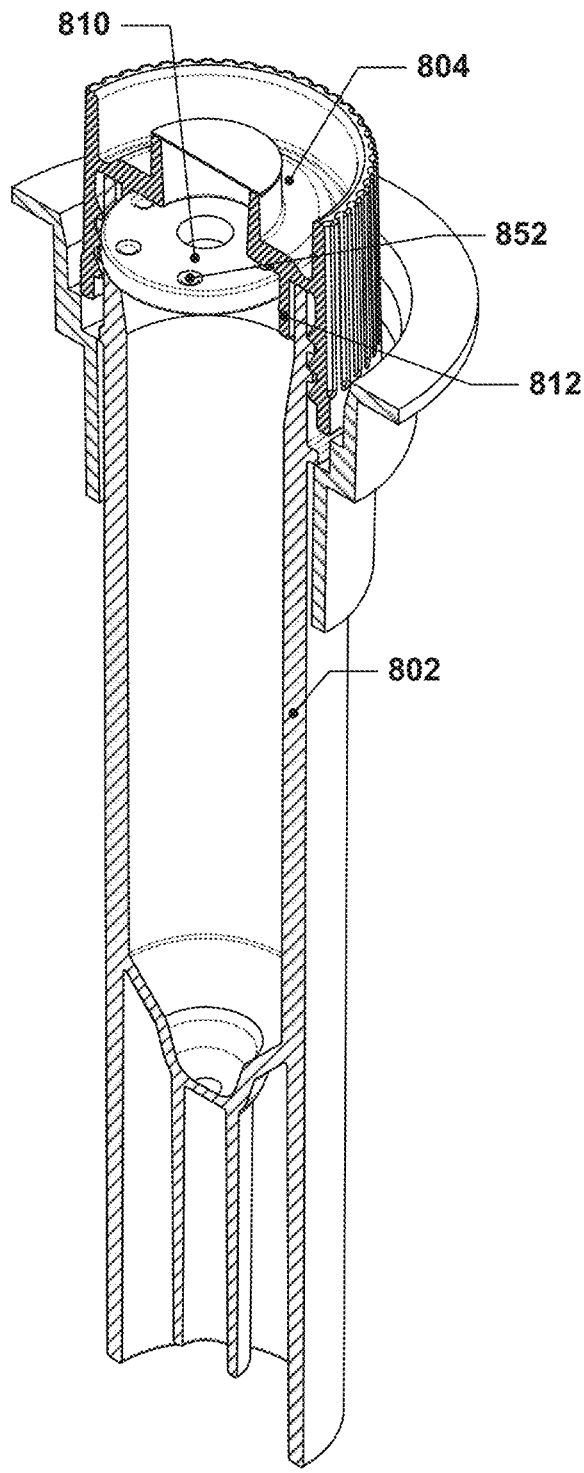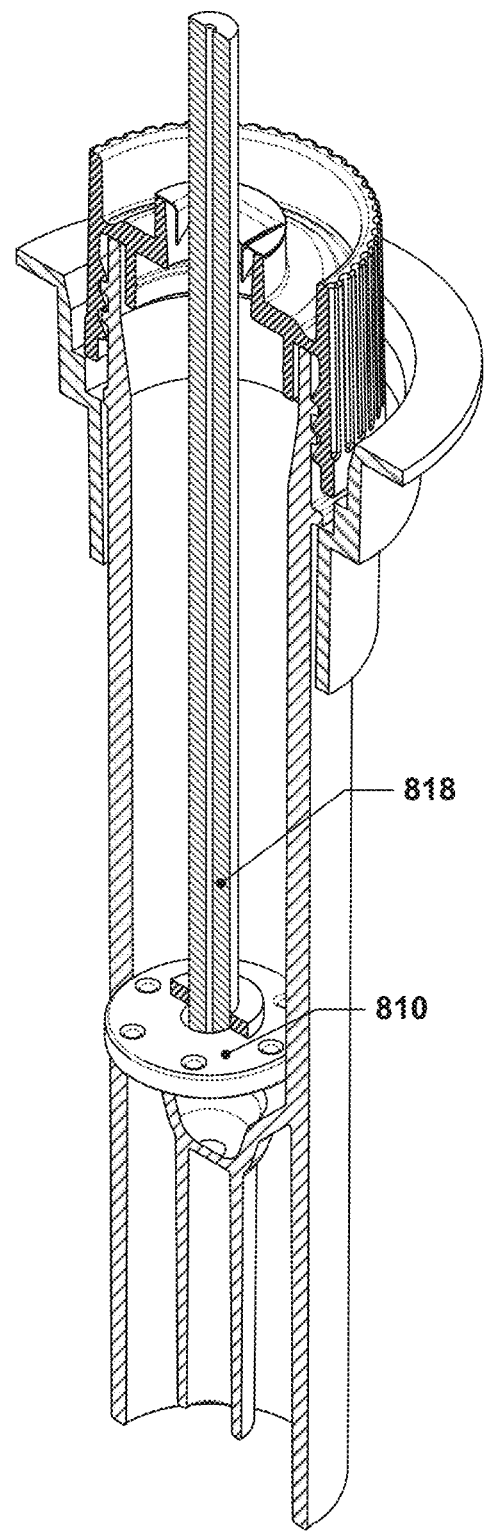
Figure 8              Figure 8'

SAMPLE TUBE WITH INTEGRATED MIXING PLUNGER HEAD

CROSS-REFERENCE TO RELATED APPLICATION

This application claims benefit of priority under 35 U.S.C. § 119(e) to U.S. Patent Application No. 62/441,921, filed Jan. 3, 2017, which is hereby incorporated by reference herein in its entirety.

BACKGROUND

In some chemical and biological analysis systems, specimen samples may often be placed into small containers, e.g., vials, that may have a fluid within them. Such samples may then be mixed with the contents of such containers in order to more evenly disperse or distribute the sample within the fluid and/or to promote a complete reaction between the fluid, which may be a reagent, and the sample.

SUMMARY

Disclosed in some examples herein are concepts and techniques for implementing a new type of sample container that includes features that may be used to provide enhanced mixing of materials contained within the sample containers.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, an apparatus may be provided with a cap having a capping surface and one or more sidewalls extending away from the capping surface along a direction having a major component that is parallel to a normal of the capping surface. The apparatus may also include a plunger head that is sized to fit within an interior of a container with which the cap is to, or is configured to, interface. The apparatus may further include a retaining feature and an opening in the cap. The plunger head may include a shaft-receiving feature to, or configured to, receive a shaft that is insertable through the opening, the plunger head may be positioned within the cap by the retaining feature such that the opening is aligned with the shaft-receiving feature, and the retaining feature may release the plunger head when a force higher than a first threshold amount is applied to the plunger head in a direction facing away from, and normal to, the capping surface.

In some implementations, the plunger head may be a circular disk and/or made of an elastomeric material.

In some implementations, the retaining feature may have one or more interior-facing surfaces that compress the plunger head radially when the plunger head is inserted into the retaining feature.

In some implementations, the retaining feature may have one or more interior-facing surfaces and one or more ledge surfaces that extend radially inwards from the one or more interior-facing surfaces, and the one or more ledge surfaces may have one or more innermost edges that are within a prismatic volume bounded by an outermost perimeter of the plunger head and extending along an axis that is parallel to the normal of the capping surface.

In some implementations, the one or more interior-facing surfaces may define an inner perimeter that is larger than the plunger head, thereby allowing the plunger head to translate laterally at least some amount when positioned within the retaining feature.

In some implementations, the one or more sidewalls may be a single circular sidewall. In some such implementations, an interior surface of the circular sidewall may include thread features to, or configured to, engage with corresponding thread features on an exterior surface of the container with which the cap is to, or is configured to, interface.

In some implementations, the apparatus may further include a perforable seal that seals the opening in the cap and is perforable by the shaft when the shaft is inserted through the opening.

In some implementations, the shaft-receiving feature may be a hole that is sized to be smaller in diameter than a maximum dimension of the shaft in a direction that is perpendicular to the normal to the capping surface when the shaft is aligned with the normal to the capping surface.

In some implementations, the apparatus may further include the container. In such implementations, the cap may be mounted to the container and the interior of the container may be sized to allow the plunger head to be reciprocated within the interior of the container in a direction parallel to the normal of the capping surface. In some such implementations, the container may have a portion with a substantially constant cross section, e.g., with less than about 1 to 2 degrees of taper, along the direction parallel to the normal of the capping surface. In some implementations, the apparatus may further include the shaft. In such implementations, the shaft may have a center axis that is parallel to the normal of the capping surface when the shaft is inserted through the opening, the shaft may have an insertion portion and a stop portion. The insertion portion may extend from one end of the shaft to the stop portion, the stop portion may be sized larger than the insertion portion in a direction perpendicular to the center axis and may also be sized larger than the shaft-receiving feature in the direction perpendicular to the center axis, and the stop portion may engage with the plunger head when the insertion portion is fully inserted into the shaft-receiving feature. In some such implementations, the apparatus may further include a shaft reciprocation mechanism that may be to, or may be configured to, translate the shaft through the opening along the center axis such that the insertion portion is fully inserted into the shaft-receiving feature, apply a force of at least the first threshold amount to the shaft, and reciprocate the shaft one or more times within the interior of the container. In some implementations, the shaft may be a hollow tube.

In some implementations, a method may be provided that includes inserting an insertion portion of a shaft through an opening in a cap of a container and into a shaft-receiving feature in a plunger head that is positioned within the cap by a retaining feature, applying a force greater than a first threshold amount to the shaft after the insertion portion is fully inserted into the shaft-receiving feature, thereby causing the retaining feature to release the plunger head, and reciprocating the shaft, after the plunger head has been released from the retaining feature, such that the plunger head is reciprocated within an interior volume of the container.

In some implementations of the method, the method may further include piercing a perforable seal in the cap with the insertion portion prior to inserting the insertion portion into the shaft-receiving feature.

In some implementations of the method, the method may also include withdrawing the insertion portion from the container, thereby causing the plunger head to engage with the cap and be pushed off the insertion portion by the cap.

These and other implementations are described in further detail with reference to the Figures and the detailed description below. Other features, aspects, and advantages will become apparent from the description, the drawings, and the claims. Note that the relative dimensions of the following figures may not be drawn to scale.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIG. 1' depicts a section view of the example vial of FIG. 1.

FIG. 1" depicts an isometric section view of the example vial of FIG. 1.

FIG. 3 depicts a section view of the example vial of FIG. 1 after being punctured by a sampling probe.

FIG. 3' depicts an isometric section view of the example vial of FIG. 3.

FIG. 4 depicts a section view of the example vial of FIG. 3 after the sampling probe has been fully inserted into the vial.

FIG. 4' depicts an isometric section view of the example vial of FIG. 4.

FIG. 6' depicts an isometric view of the example vial of FIG. 6 with a shaft inserted and the plunger head deployed.

FIG. 6" depicts a section view of the example vial of FIG. 6'.

FIG. 7 depicts an isometric cutaway view of another example vial with an integrated plunger head.

FIG. 7' depicts an isometric view of the example vial of FIG. 7 with a shaft inserted and the plunger head deployed.

FIG. 8 depicts an isometric cutaway view of another example vial with an integrated plunger head.

FIG. 8' depicts an isometric view of the example vial of FIG. 8 with a shaft inserted and the plunger head deployed.

DETAILED DESCRIPTION

Importantly, the present disclosure is neither limited to any single aspect nor implementation, nor to any combinations and/or permutations of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein.

Provided in examples herein is a sample vial that may be used with systems having sampling probes or "sippers" that are insertable into the vial. Such sample vials may be used in chemical or biological analysis systems to hold samples and/or reagents, and it may, in many systems, be desirable to mix the ingredients of such sample vials prior to withdrawing the contents for analysis. Disclosed herein is a new type of cap that may be used with sample vials in order to provide a highly effective mixing system.

In general, such caps may include a separable plunger head that is retained by features on the cap but that may be released by the cap upon the application of sufficient force. The plunger head may have a diameter that is smaller than the interior diameter of the container of the sample vial to allow fluid within the container to flow past the plunger head as the plunger head is reciprocated within the sample vial. Alternatively, the plunger head may have the same diameter as (or one slightly larger than) the interior diameter of the container—however, the plunger head, in such instances, may also include through-holes, exterior channels, etc. to allow the fluid to flow past the plunger head as the plunger head is reciprocated within the container. The plunger head may be located on the interior-facing side of the cap, and the cap may have an opening through which the shaft of a sampling probe or sipper may be inserted in order to push on the plunger head and provide the force sufficient to release the plunger head from the cap. The plunger head may have a shaft-receiving feature that interfaces with the shaft of the sampling probe such that the plunger head becomes connected to the sampling probe and moves with the sampling probe within the container once released from the cap. Once the plunger head is connected with the sampling probe, the sampling probe with attached plunger head may be reciprocated within the interior volume of the container, which may act to mix the contents of the container.

Figure 1:
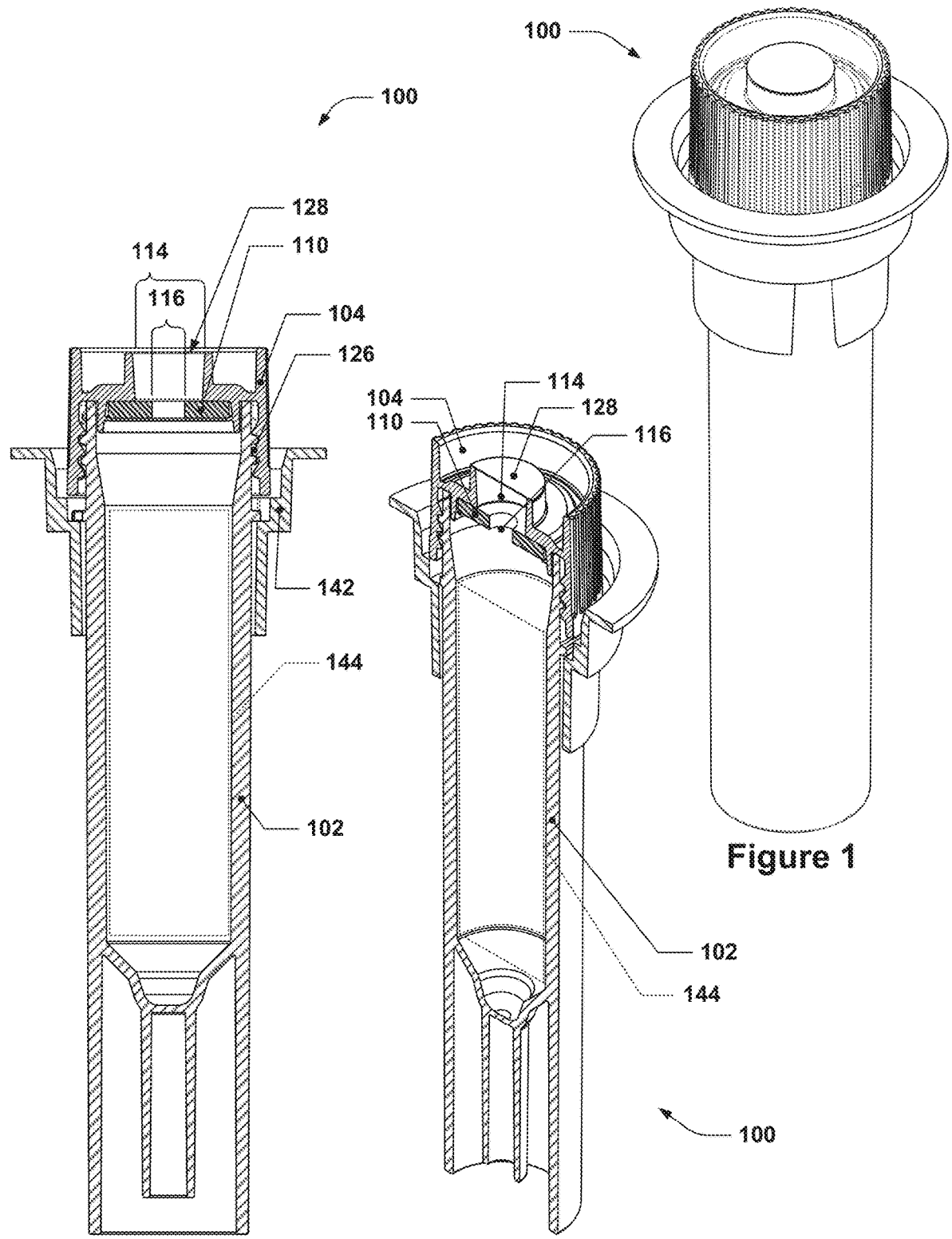
FIG. 1 depicts an isometric view of an example vial.
Figure 2:
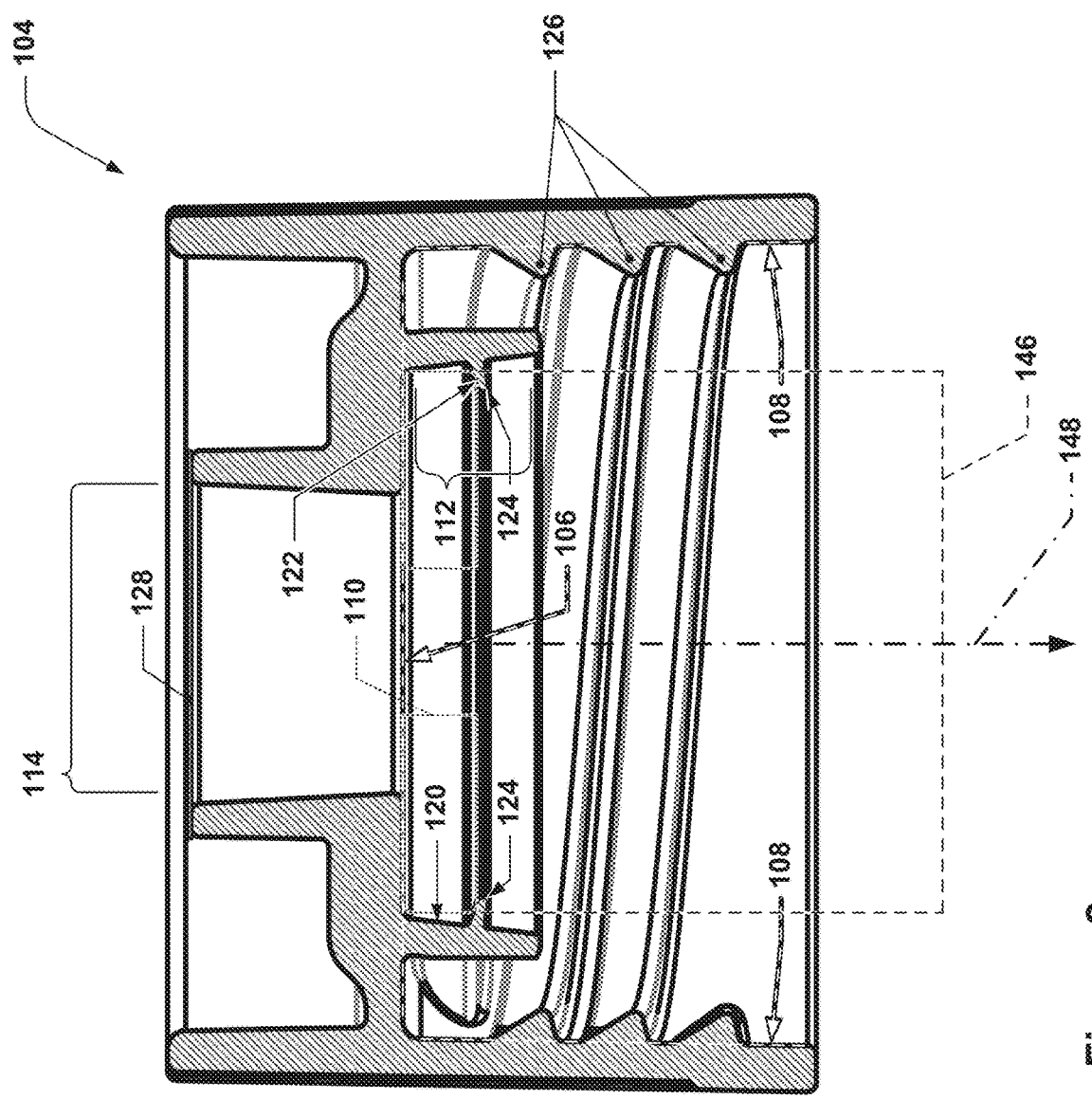
FIG. 2 depicts a section view of the cap of the example vial of FIG. 1.

FIG. 1 depicts an isometric view of an example vial, FIG. 1' depicts a section view of the example vial of FIG. 1, and FIG. 1" depicts an isometric section view of the example vial of FIG. 1. FIG. 2 depicts a detail section view of the cap of the example vial of FIG. 1.

Depicted in FIGS. 1-1" are a vial 100 that has a cap 104 and a container 102; the vial 100 may be sized to fit within a receptacle 142 that holds the vial 100 during mixing operations. The cap 104 may have a capping surface 106 (see FIG. 2) that generally faces towards the interior of the container 102 and that acts to wall off the open end of the container that the cap is fastened to; the cap 104 may also have a sidewall or sidewalls 108 that face inwards and extend away from the capping surface 106 in directions substantially perpendicular to the capping surface 106 (in this case, there is a slight taper to the sidewall 108, and "substantially perpendicular" in this context may be understood to refer to sidewalls that are within ±10° of perpendicular; the sidewall may also be thought of as extending away from the capping surface along a direction having a major component 148 that is perpendicular to the capping surface). In the example implementation, there is a single, circular sidewall 108. The cap 104, however, has an opening 114 that passes through the capping surface 106 to allow a probe or sipper shaft to be inserted through the cap 104 and into the interior of the container 102 without requiring removal of the cap 104. In some implementations, the opening 114 may be sealed with a perforable seal 128, such as a foil induction seal or other membrane, to prevent potential leaks or contamination of the fluid within the container 102.

The cap 104 may have retained within it a plunger head 110. The plunger head 110 may be retained within the cap 104 by a retaining feature 112. In this example, the retaining feature 112 consists of an annular wall with an interior-facing surface 120 that has one or more ledge surfaces 122 projecting radially inwards from it. The ledge surface or surfaces 122 may provide innermost edges 124 that are slightly smaller, e.g., about 0.2 to about 0.5 mm, than the outermost diameter of the plunger head 110, thereby preventing the plunger head 110 from falling out of the cap 104. Put another way, the innermost edge or edges 124 may be within a prismatic volume 146 that is defined by the outermost perimeter of the plunger head 110 and that extends along the direction 148 that is normal to the capping surface 106. However, if sufficient force is applied to the plunger head 110 along a direction generally perpendicular to the capping surface 106 and towards the container 102, the plunger head 110 may be forced past the ledge surface 122 and into the container 102. For example, the plunger head 110 may force the ledge to deform and cause the innermost diameter of the ledge surface 122 to expand and/or the plunger head 110 may itself compress to reduce the outermost diameter of the plunger head 110 in order to allow the plunger head 110 to escape the retaining feature 112. In some implementations, the interior-facing surface or surfaces 120 may define an inner perimeter that is larger than the outermost perimeter of the plunger head 110, thereby allowing the plunger head 110 to float within the cap 104 while still being retained by a ledge-type retaining feature 112.

The plunger head 110 may include a shaft retaining feature 116 that acts to receive an insertion portion of a shaft, e.g., of a probe or a sipper. The shaft retaining feature 116 may be slightly smaller in size than the outer perimeter of the shaft that is intended to be inserted therein, thereby creating a press fit between the shaft and the shaft retaining feature 116.

The cap 104 may be fastened to the container 102 using thread features 126, although other types of connections may be used as well, such as friction/press-fit connections, bayonet-style connections, or barbed, single use connections that are tamper-resistant.

FIG. 3 depicts a section view of the example vial of FIG. 1 after being punctured by a sampling probe, FIG. 3' depicts an isometric section view of the example vial of FIG. 3, FIG. 4 depicts a section view of the example vial of FIG. 3 after the sampling probe has been fully inserted into the vial, and FIG. 4' depicts an isometric section view of the example vial of FIG. 4. As discussed above, the vial 100 may be inserted into a receptacle 142 for mixing operations. A sample probe with a shaft 118 may then be lowered into the cap 104, e.g., by a shaft reciprocation system 134. In implementations with a perforable seal 128, the shaft 118 may be inserted through the perforable seal 128, thereby breaking the seal. The shaft 118 may then be inserted further into the cap 104 such that an insertion portion 130 of the shaft, e.g., the tip, is inserted into the shaft-receiving feature 116 of the plunger head 110. As discussed earlier, the shaft-receiving feature 116 may be sized so as to press-fit with the shaft 118. The retaining feature(s) 112 may be sized such that the amount of force that is required to free the plunger head 110 from the retaining feature(s) 112 is greater than the amount of force required to insert the insertion portion 130 into the shaft-receiving feature 116. This ensures that the plunger head 110 is not ejected from the retaining feature(s) 112 before the plunger head 110 is press fit onto the shaft 118. The shaft 118 may also have a stop portion 132, e.g., a swaged or brazed ferrule or bushing, that is a larger diameter than then shaft-receiving feature. The stop portion 132 may butt up against the plunger head 110 when the insertion portion 130 is fully inserted into the shaft-receiving feature 116. Once the stop portion 132 is engaged with the plunger head 110, then generally all of the downward force that is applied to the shaft 118 may be transferred to the plunger head 110 and used to force the plunger head 110 to disengage from the retaining feature 112. Once the plunger head 110 is disengaged from the retaining feature 112, the shaft reciprocation mechanism 134 may be used to move the shaft 118 up and down within the container 102 such that the plunger head 110 is reciprocated within the interior 144 of the container 102. Any fluids that are present within the interior volume 144 may thus be forced to flow back and forth past the plunger head 110, thereby ensuring adequate mixing. Between 4 and 7 reciprocations (up/down motions) was found to provide sufficient mixing in many sample test cases.

Once the contents of the container 102 have been thoroughly mixed by reciprocating the plunger head within the container 102, the shaft 118 may be extended such that the insertion portion 130 is located at the bottom of the container 102. Fluid that has collected at the bottom of the container 102 may be drawn up through the shaft 118, e.g., by a pump or other suction-generating device. Once sufficient fluid has been withdrawn from the container 102, the shaft 118 may be withdrawn from the container 102. During such withdrawal, the plunger head 110 may contact the retaining feature(s) 112, which may prevent the plunger head 110 from further movement, thus causing the plunger head 110 to separate from the shaft 118 and fall back into the container 102. In some implementations, the plunger head 110 may be re-captured by the retaining feature 112 or a portion thereof so that the plunger head 110 still separates from the shaft 118 but does not fall back into the container 102.

The plunger head 110 may be made from a plastic or other polymeric material, such as a stiff elastomer. This may allow the plunger head 110 to be somewhat compliant, allowing it to flex and compress as it is freed from the retaining feature 112, and may also allow the plunger head to easily expand to accommodate the press fit of the shaft 118.

Figure 5:
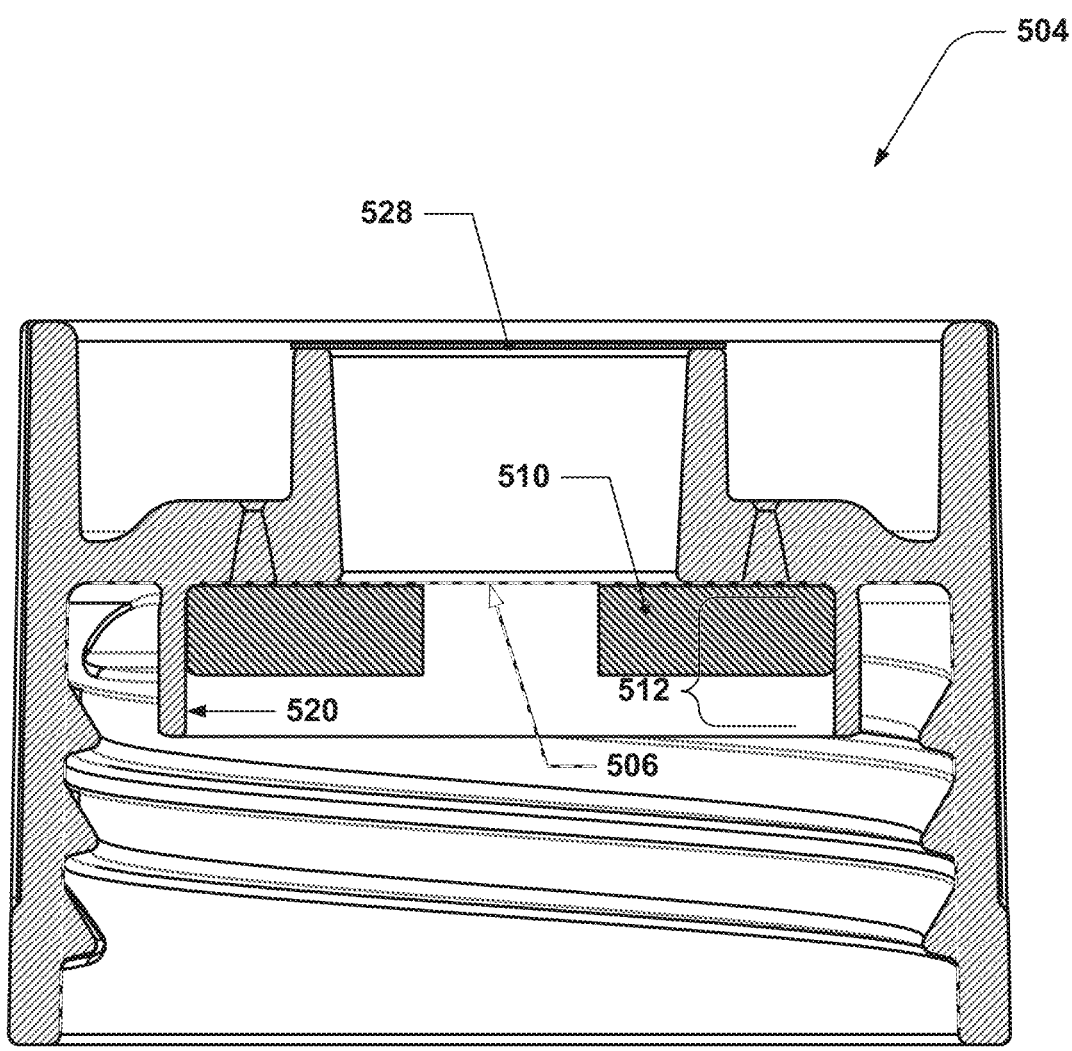
FIG. 5 depicts a section view of an alternate example cap.

FIG. 5 depicts a section view of an alternate example cap. In this view, cap 504's retaining feature 512 has no ledge surface and is instead provided by a circular wall with interior-facing surfaces 520 that are sized slightly smaller in interior diameter than the external diameter of plunger head 510, thereby holding the plunger head 510 in place through compression and friction.

Figure 6:
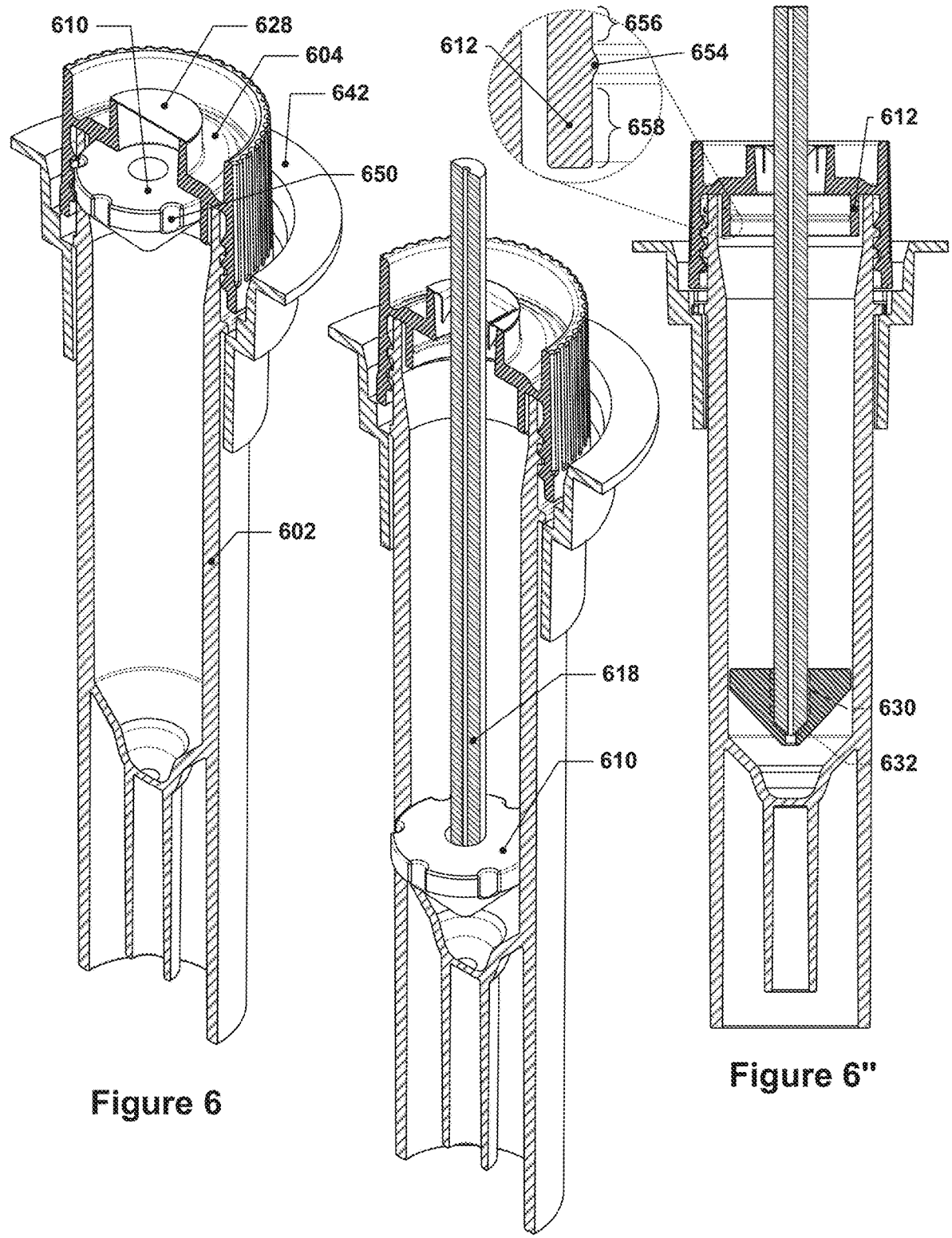
FIG. 6 depicts an isometric cutaway view of another example vial with an integrated plunger head.

FIG. 6 depicts an isometric cutaway view of another example vial with an integrated plunger head. FIG. 6' depicts an isometric view of the example vial of FIG. 6 with a shaft inserted and the plunger head deployed. FIG. 6" depicts a section view of the sample vial of FIG. 6'.

In FIGS. 6 through 6", a vial is shown with a container 602 and a cap 604. The cap 604 has a plunger head 610 that is retained within the cap 604 by a retaining feature 612 that has cylindrical interior-facing surfaces that are sized so that the plunger head 612 is a light press fit into the retaining feature 612. Additionally, the retaining feature 612 may have a circular ridge 654 that narrows the retaining feature 612 even further. This circular ridge 654 requires that additional force be applied to the plunger head 610 in order to break it free from the retaining feature 612 beyond the force that is required to break the plunger head 610 free from the press fit alone. Thus, the circular ridge 654 retains the plunger head during insertion of the insertion portion 630 of the shaft 618, and the shaft 618 then pushes the plunger head past the circular ridge 654 when the stop portion 632 of the shaft 618 butts up against an interior ledge/surface of the shaft-receiving feature in the plunger head 610. The plunger head 610 is then reciprocated within the container 602. When the shaft 618 is removed from the container 602, the plunger head 610 may re-engage with the retaining feature 612 and, in some implementations, may re-engage with a lower portion 658 of the retaining feature 612, which is separated from an upper portion 656 of the retaining feature 612 by the circular ridge 654. The retaining feature 612 may thus re-capture the plunger head 610 upon withdrawal of the shaft 618.

In this implementation, the plunger head 610 has a plurality of grooves or channels 650 around the exterior perimeter to allow for enhanced fluid flow past the plunger head 610 during mixing.

FIG. 7 depicts an isometric cutaway view of another example vial with an integrated plunger head. FIG. 7' depicts an isometric view of the example vial of FIG. 7 with a shaft inserted and the plunger head deployed. In FIGS. 7 and 7', a vial very similar to that shown in FIGS. 6 through 6" is shown, except that the plunger head 710 has no grooves in it, and the retaining feature 712 does not have the circular ridge and instead relies on a tighter press fit with the plunger head 710.

FIG. 8 depicts an isometric cutaway view of another example vial with an integrated plunger head. FIG. 8' depicts an isometric view of the example vial of FIG. 8 with a shaft inserted and the plunger head deployed. In FIGS. 8 and 8', the plunger head 810 has a pattern of through-holes 852 that allow for fluid to flow through the plunger head 810 during reciprocation of the plunger head 810. The cap 804 also has a retaining feature 812 that is similar to that shown in FIG. 7. Otherwise, the vial shown in FIGS. 8 and 8' is similar to the vial shown in FIGS. 1 through 4.

The terms "substantially" and "about" used throughout this disclosure, including the claims, are used to describe and account for small fluctuations, such as due to variations in processing. For example, unless otherwise specified herein in a particular context, they can refer to less than or equal to ±5%, of the specified value or value equivalent to the specified relationship, such as less than or equal to ±2%, such as less than or equal to ±1%, such as less than or equal to ±0.5%, such as less than or equal to ±0.2%, such as less than or equal to ±0.1%, such as less than or equal to ±0.05%. For example, "substantially perpendicular" may be used to refer to a geometric relationship in which the angle between two surfaces is within ±5% (or, alternatively, one of the other bounding ranges listed above) of 90°.

The use, if any, of ordinal indicators, e.g., (a), (b), (c) . . . or the like, in this disclosure and claims is to be understood as not conveying any particular order or sequence, except to the extent that such an order or sequence is explicitly indicated. For example, if there are three steps labeled (i), (ii), and (iii), it is to be understood that these steps may be performed in any order (or even concurrently, if not otherwise contraindicated) unless indicated otherwise. For example, if step (ii) involves the handling of an element that is created in step (i), then step (ii) may be viewed as happening at some point after step (i). Similarly, if step (i) involves the handling of an element that is created in step (ii), the reverse is to be understood.

It is also to be understood that the use of "to," e.g., "with which the cap is to interface," may be replaceable with language such as "configured to," e.g., "with which the cap is configured to interface", or the like.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. For the sake of brevity, many of those permutations and combinations will not be discussed and/or illustrated separately herein.

What is claimed is:

1. An apparatus comprising:
   a cap with a capping surface and one or more sidewalls extending away from the capping surface along a direction having a major component that is parallel to a normal of the capping surface;
   a plunger head, the plunger head sized to fit within an interior of a container with which the cap is to interface;
   a retaining feature; and
   an opening in the cap, wherein:
      the plunger head includes a shaft-receiving feature to receive a shaft that is insertable through the opening,
      the shaft-receiving feature is a hole that extends through the plunger head,
      the plunger head is positioned within the cap by the retaining feature such that the opening is aligned with the shaft-receiving feature, and
      the retaining feature releases the plunger head when a force higher than a first threshold amount is applied to the plunger head in a direction facing away from, and normal to, the capping surface.

2. The apparatus of claim 1, wherein the plunger head is a circular disk.

3. The apparatus of claim 2, wherein the plunger head is made of an elastomeric material.

4. The apparatus of claim 1, wherein the retaining feature has one or more interior-facing surfaces that compress the plunger head radially when the plunger head is inserted into the retaining feature.

5. The apparatus of claim 1, wherein:
   the retaining feature has one or more interior-facing surfaces and one or more ledge surfaces that extend radially inwards from the one or more interior-facing surfaces, and
   the one or more ledge surfaces have one or more innermost edges that are within a prismatic volume bounded by an outermost perimeter of the plunger head and extending along an axis that is parallel to the normal of the capping surface.

6. The apparatus of claim 5, wherein the one or more interior-facing surfaces define an inner perimeter that is larger than the plunger head, thereby allowing the plunger head to translate laterally at least some amount when positioned within the retaining feature.

7. The apparatus of claim 1, wherein the one or more sidewalls is a single circular sidewall.

8. The apparatus of claim 7, wherein an interior surface of the circular sidewall includes thread features to engage with corresponding thread features on an exterior surface of the container with which the cap is to interface.

9. The apparatus of claim 1, further comprising a perforable seal that is affixed to the cap and seals the opening in the cap, and that is perforable by the shaft when the shaft is inserted through the opening.

10. The apparatus of claim 1, wherein the shaft-receiving feature is sized to be smaller in diameter than a maximum dimension of the shaft in a direction that is perpendicular to the normal to the capping surface when the shaft is aligned with the normal to the capping surface.

11. The apparatus of claim 1, further comprising the container, wherein:
   the cap is mounted to the container, and the interior of the container is sized to allow the plunger head to be reciprocated within the interior of the container in a direction parallel to the normal of the capping surface.

12. The apparatus of claim 11, wherein the container has a portion with a substantially constant cross section along the direction parallel to the normal of the capping surface.

13. The apparatus of claim 11, further comprising the shaft, wherein:
the shaft has a center axis that is parallel to the normal of the capping surface when the shaft is inserted through the opening,
the shaft has an insertion portion and a stop portion,
the insertion portion extends from one end of the shaft to the stop portion,
the stop portion is sized larger than the insertion portion in a direction perpendicular to the center axis and is also sized larger than the shaft-receiving feature in the direction perpendicular to the center axis, and
the stop portion engages with the plunger head when the insertion portion is fully inserted into the shaft-receiving feature.

14. The apparatus of claim 13, further comprising a shaft reciprocation mechanism, wherein the shaft reciprocation mechanism is to:
translate the shaft through the opening along the center axis such that the insertion portion is fully inserted into the shaft-receiving feature,
apply a force of at least the first threshold amount to the shaft, and
reciprocate the shaft one or more times within the interior of the container.

15. The apparatus of claim 13, wherein the shaft is a hollow tube.

16. A method comprising:
inserting an insertion portion of a shaft through an opening in a cap of a container and into a shaft-receiving feature in a plunger head that is positioned within the cap by a retaining feature, wherein the shaft-receiving feature is a hole extending through the plunger head;
applying a force greater than a first threshold amount to the shaft after the insertion portion of the shaft is fully inserted into the shaft-receiving feature of the plunger head, thereby causing the retaining feature to release the plunger head; and
reciprocating the shaft, after the plunger head has been released from the retaining feature, such that the plunger head is reciprocated within an interior volume of the container.

17. The method of claim 16, further comprising piercing a perforable seal in the cap with the insertion portion prior to inserting the insertion portion into the shaft-receiving feature.

18. The method of claim 16, further comprising withdrawing the insertion portion from the container, thereby causing the plunger head to engage with the cap and be pushed off the insertion portion by the cap.

19. The apparatus of claim 1, wherein the hole that extends through the plunger head extends in a direction parallel to the normal of the capping surface.

20. An apparatus comprising:
a cap with a capping surface and one or more sidewalls extending away from the capping surface along a direction having a major component that is parallel to a normal of the capping surface;
a plunger head, the plunger head having an outer diameter and sized to fit within an interior of a container with which the cap is to interface;
a retaining feature; and
an opening in the cap, wherein:
the plunger head includes a shaft-receiving feature to receive a shaft that is insertable through the opening,
the shaft-receiving feature is a hole that extends through the plunger head,
the plunger head is positioned within the cap by the retaining feature such that the opening is aligned with the shaft-receiving feature,
the retaining feature releases the plunger head when a force higher than a first threshold amount is applied to the plunger head in a direction facing away from, and normal to, the capping surface, and
a largest dimension of the plunger head is larger than a smallest dimension of the opening in the cap.

* * * * *